US007919572B2

(12) United States Patent
Angot et al.

(10) Patent No.: US 7,919,572 B2
(45) Date of Patent: Apr. 5, 2011

(54) POLYAMINO ACIDS FUNCTIONALISED WITH AT LEAST ONE HYDROPHOBIC GROUP AND APPLICATIONS THEREOF PARTICULARLY THERAPEUTIC APPLICATIONS

(75) Inventors: Stéphanie Angot, Gradignan (FR); Olivier Breyne, Lyons (FR); You-Ping Chan, Lyons (FR)

(73) Assignee: Flamel Technologies, Venissieux (FR)

( * ) Notice: Subject to any disclaimer, the term of this patent is extended or adjusted under 35 U.S.C. 154(b) by 0 days.

(21) Appl. No.: 10/558,617

(22) PCT Filed: May 28, 2004

(86) PCT No.: PCT/FR2004/050209
§ 371 (c)(1),
(2), (4) Date: Sep. 18, 2006

(87) PCT Pub. No.: WO2004/108796
PCT Pub. Date: Dec. 16, 2004

(65) Prior Publication Data
US 2007/0010652 A1     Jan. 11, 2007

(30) Foreign Application Priority Data
May 28, 2003  (FR) ...................................... 03 50190

(51) Int. Cl.
*C08G 69/10*  (2006.01)
*A01N 25/00*  (2006.01)
*A61K 47/00*  (2006.01)

(52) U.S. Cl. ........................................ 528/328; 514/773
(58) Field of Classification Search .................. 528/328; 514/773
See application file for complete search history.

(56) References Cited

U.S. PATENT DOCUMENTS

| | | | |
|---|---|---|---|
| 2,680,749 A | 6/1954 | Cawley et al. | |
| 4,126,628 A | 11/1978 | Paquet | |
| 4,351,337 A | 9/1982 | Sidman | |
| 4,600,526 A | 7/1986 | Gallot et al. | |
| 4,652,441 A | 3/1987 | Okada et al. | |
| 4,766,106 A | 8/1988 | Katre et al. | |
| 4,826,818 A | 5/1989 | Mori et al. | |
| 4,888,398 A | 12/1989 | Bichon et al. | |
| 4,892,733 A | 1/1990 | Bichon et al. | |
| 5,102,872 A | 4/1992 | Singh et al. | |
| 5,399,331 A | 3/1995 | Loughrey et al. | |
| 5,449,513 A | 9/1995 | Yokoyama et al. | |
| 5,534,241 A | 7/1996 | Torchilin et al. | |
| 5,609,872 A | 3/1997 | Ahlborg et al. | |
| 5,747,635 A * | 5/1998 | Kroner et al. | 528/328 |
| 5,760,163 A * | 6/1998 | Fisch et al. | 528/310 |
| 5,766,633 A * | 6/1998 | Milstein et al. | 424/489 |
| 5,792,451 A * | 8/1998 | Sarubbi et al. | 424/85.4 |
| 5,854,378 A * | 12/1998 | Tomida et al. | 528/328 |
| 5,863,900 A | 1/1999 | Russell-Jones | |
| 5,869,703 A | 2/1999 | Kim et al. | |
| 5,872,210 A | 2/1999 | Medabalimi | |
| 5,876,969 A | 3/1999 | Fleer et al. | |
| 5,904,936 A | 5/1999 | Huille et al. | |
| RE36,234 E * | 6/1999 | Koskan et al. | 528/363 |
| 5,929,198 A * | 7/1999 | Tang | 528/288 |
| 5,981,761 A | 11/1999 | Chou et al. | |
| 5,998,545 A * | 12/1999 | Melot et al. | 525/178 |
| 6,143,314 A | 11/2000 | Chandrashekar et al. | |
| 6,153,193 A | 11/2000 | Kabanov et al. | |
| 6,197,535 B1 | 3/2001 | Bandyopadhyay et al. | |
| 6,201,072 B1 | 3/2001 | Rathi et al. | |
| 6,235,282 B1 | 5/2001 | Riviere et al. | |
| 6,284,267 B1 | 9/2001 | Aneja | |
| 6,291,634 B1 * | 9/2001 | Tanaka et al. | 528/328 |
| 6,313,095 B1 | 11/2001 | Adams et al. | |
| 6,313,260 B2 | 11/2001 | Gruning et al. | |
| 6,320,017 B1 | 11/2001 | Ansell | |
| 6,355,270 B1 * | 3/2002 | Ferrari et al. | 424/489 |
| 6,355,771 B1 * | 3/2002 | Oda | 528/328 |
| 6,428,780 B2 * | 8/2002 | Leone-Bay et al. | 424/85.1 |

(Continued)

FOREIGN PATENT DOCUMENTS

CN     1 282 345     1/2001

(Continued)

OTHER PUBLICATIONS

Nukui, Masahiro; Hoes, Kees; Van den Berg, Hans; Feijen, Jan; Association of macromolecular prodrugs consisting of adriamycin bound to poly(L-glutamic acid), Makromolekulare Chemie, 192(12), pp. 2925-2942.*
In the U.S. Patent and Trademark Office, Final Office Action in re: U.S. Appl. No. 10/516,733, dated Jun. 17, 2008, 8 pages.
In the U.S. Patent and Trademark Office, Non-Final Office Action in re: U.S. Appl. No. 10/516,733, dated Feb. 5, 2007, 7 pages.
In the U.S. Patent and Trademark Office, Non-Final Office Action in re: U.S. Appl. No. 10/516,733, dated Sep. 12, 2007, 7 pages.
In the U.S. Patent and Trademark Office, Non-Final Office Action in re: U.S. Appl. No. 10/516,733, dated Feb. 26, 2009, 4 pages.

(Continued)

*Primary Examiner* — Mark Eashoo
*Assistant Examiner* — Liam J Heincer
(74) *Attorney, Agent, or Firm* — Patton Boggs, LLP

(57) ABSTRACT

The invention relates to novel materials based on biodegradable polyamino acids, particularly useful for the vectorisation of active principals (PA). The invention further relates to novel, pharmaceutical, cosmetic, dietary or phytosanitary compositions. The invention provides novel polymeric raw material, for use in the vectorisation of PA and with an optimal match for all the requirements of the type: biocompatibility, biodegradability, stability, ability to easily associate with numerous active principals or to solubilise the same and to liberate said active principals in vivo. Said aim is achieved with polyamino acids comprising aspartic and/or glutamate units, some of which carry at least one graft, characterised in that at least one of said grafts is bonded to an aspartic or glutamate unit by means of an amino acids spacer based on Leu, and/or Ileu, and/or Val, and/or Phe and a hydrophobic group with C6-C30 is connected by an ester bond to the spacer.

21 Claims, No Drawings

U.S. PATENT DOCUMENTS

| | | | |
|---|---|---|---|
| 6,500,448 B1 | 12/2002 | Johnson et al. | |
| 6,559,274 B2 * | 5/2003 | Gertzmann et al. | 528/328 |
| 6,737,501 B2 * | 5/2004 | Dietz et al. | 528/328 |
| 6,774,207 B2 * | 8/2004 | Danielmeier et al. | 528/328 |
| 6,790,925 B2 * | 9/2004 | Danielmeier et al. | 528/68 |
| 6,855,770 B2 * | 2/2005 | Pinchuk et al. | 525/240 |
| 6,933,269 B2 | 8/2005 | Jordan et al. | |
| 7,030,155 B2 | 4/2006 | Lambert et al. | |
| 7,033,602 B1 * | 4/2006 | Pacetti et al. | 424/426 |
| 7,091,305 B2 * | 8/2006 | Sikes | 528/322 |
| 7,270,832 B2 | 9/2007 | Bryson et al. | |
| 7,683,024 B2 | 3/2010 | Chan et al. | |
| 2002/0077279 A1 * | 6/2002 | Kumar et al. | 514/2 |
| 2002/0169125 A1 | 11/2002 | Leung et al. | |
| 2002/0197261 A1 * | 12/2002 | Li et al. | 424/178.1 |
| 2003/0129223 A1 * | 7/2003 | Wartchow et al. | 424/450 |
| 2004/0063200 A1 * | 4/2004 | Chaikof et al. | 435/317.1 |
| 2004/0121954 A1 * | 6/2004 | Xu | 514/12 |
| 2006/0177416 A1 * | 8/2006 | Turnell et al. | 424/78.27 |

FOREIGN PATENT DOCUMENTS

| | | |
|---|---|---|
| EP | 0 179 023 A2 | 4/1986 |
| FR | 2 533 209 | 3/1984 |
| JP | 2002194078 | 7/2002 |
| JP | 2002194080 | 7/2002 |
| JP | 2003327693 A * | 11/2003 |
| WO | WO 87/02219 | 4/1987 |
| WO | WO 87/03891 | 7/1987 |
| WO | WO 96/29991 | 10/1996 |
| WO | WO 98/11874 | 3/1998 |
| WO | WO 99/18142 | 4/1999 |
| WO | WO 99/61512 | 12/1999 |
| WO | WO 00/18821 | 4/2000 |
| WO | WO 00/30618 | 6/2000 |
| WO | WO 00/71163 | 11/2000 |
| WO | WO 00/78791 | 12/2000 |
| WO | WO 00/78791 A2 | 12/2000 |
| WO | WO 02/028251 | 4/2002 |
| WO | WO 02/028521 | 4/2002 |
| WO | WO 02/098951 | 12/2002 |
| WO | WO 02/098952 | 12/2002 |
| WO | WO 03/002096 | 1/2003 |

OTHER PUBLICATIONS

Akiyoshi et al., "Self-Assembled Hydrogel Nanoparticle of Cholesterol-Bearing Pullulan as a Carrier of Protein Drugs: Complexation and Stabilization of Insulin," *J. Control. Release*, 1998; 54:313-320.

Fuller, W.D., "A Procedure for the Facile Synthesis of Amino-Acid N-Carboxyanhydrides," *Biopolymers*, 1976; 15:1869-1871.

Gonsalves et al, "Synthesis and Surface Characterization of Functionalized Polylactide Copolymer Microparticles," *Biomaterials*, 1998; 19:1501-1505.

Hoes et al., "Optimization of Macromolecular Prodrugs of the Antitumor Antibiotic Adriamycin," *J. Controlled Release*, 1985; 2:205-213.

Hudecz et al., "Branched Polypeptides with a Poly-(L-Lysine) Backbone: Synthesis, Conformation, and Immunomodulation," *Polymeric Materials in Medication*, Plenum Press, New York, 1985; pp. 265-289.

Mezo et al., "Synthesis and Conformational Studies of Poly(L-Lysine) Based Branched Polypeptides with Ser and Glu/Leu in the Side Chains," *J. Controlled Release*, 2000; 63:81-95.

Sohn et al., "Self-Assembly of Substituted Polyglutamates on Solid Substrates: The Side-Chain Effect," *Langmuir*, 1999; 15:1698-1702.

Tomida et al., "Convenient Synthesis of High Molecular Weight Poly(succinimide) by Acid-Catalysed Polycondensation of L-aspartic Acid," *Polymer*, 1997; 38(18): 4733-4736.

Van Heeswijk et al., "The Synthesis and Characterization of Polypeptide-Adriamycin Conjugates and its Complexes with Adriamycin," *J. Controlled Release*, 1985; 1:301-315.

Volgler et al., *Helv. Chim. Acta*, 1964; 47: 525-544; English Language Summary on p. 525.

Wang et al, "Identification of the Major Positional Isomer of Pegylated Interferon Alpha-2b," *Biochemistry*, 2000; 39:10634-10640.

* cited by examiner

POLYAMINO ACIDS FUNCTIONALISED WITH AT LEAST ONE HYDROPHOBIC GROUP AND APPLICATIONS THEREOF PARTICULARLY THERAPEUTIC APPLICATIONS

The present invention relates to novel materials based on biodegradable polyamino acids that are useful especially for the vectorization of active principle(s) (AP).

The invention further relates to novel pharmaceutical, cosmetic, dietetic or phytosanitary compositions based on these polyamino acids. These compositions can be of the type allowing the vectorization of AP and preferably taking the form of emulsions, micelles, particles, gels, implants or films.

The AP in question are advantageously biologically active compounds which can be administered to an animal or human organism by the oral, parenteral, nasal, vaginal, ocular, subcutaneous, intravenous, intramuscular, intradermal, intraperitoneal, intracerebral, buccal or other route.

The AP to which the invention relates more particularly, but without implying a limitation, are proteins, glycoproteins, peptides, polysaccharides, lipopolysaccharides, oligonucleotides or polynucleotides, and organic molecules. However, they can also be cosmetic products or phytosanitary products such as herbicides, insecticides, fungicides, etc.

In the field of the vectorization of active principles, especially medicinal active principles, there is a need in many cases to:

protect them from degradation (hydrolysis, precipitation at the site, enzymatic digestion, etc.) until they reach their site of action, and/or control their rate of release so as to maintain a therapeutic level over a defined period, and/or transport . . . (with protection) to the site of action.

For these purposes, several types of polymers have been studied and some are even commercially available. Examples which may be mentioned are polymers of the polylactic, polylactic-glycolic, polyoxyethylene-oxypropylene, polyamino acid or polysaccharide type. These polymers constitute starting materials for the manufacture of e.g. mass implants, microparticles, nanoparticles, vesicles, micelles or gels. In addition to the fact that these polymers have to be suitable for the manufacture of such systems, they must also be biocompatible, non-toxic, non-immunogenic and economic and they must be easy to eliminate from the body and/or biodegradable. On this last point, it is further essential that biodegradation in the organism generates non-toxic products.

Various patents, patent applications or scientific articles are referred to below in order to illustrate the prior art relating to polymers employed as starting materials for the preparation of AP vectorization systems.

U.S. Pat. No. 4,652,441 describes polylactide microcapsules encapsulating the hormone LH-RH. These microcapsules are produced by preparing a water-in-oil-in-water emulsion and comprise an aqueous inner layer containing the hormone, a substance (gelatin) for fixing the latter, an oily polylactide layer and an aqueous outer layer (polyvinyl alcohol). The AP can be released over a period of more than two weeks after subcutaneous injection.

U.S. Pat. No. 6,153,193 describes compositions based on amphiphilic poly(oxyethylene)-poly(oxypropylene) micelles for the vectorization of anticancer agents such as adriamycin.

Akiyoshi et al. (J. Controlled Release 1998, 54, 313-320) describe pullulans which are rendered hydrophobic by the grafting of cholesterol and form nanoparticles in water. These nanoparticles, which are capable of complexing reversibly with insulin, form stable colloidal suspensions.

U.S. Pat. No. 4,351,337 describes amphiphilic copolyamino acids based on leucine and glutamate which can be used in the form of implants or microparticles for the controlled release of active principles. The latter can be released over a very long period, depending on the rate of degradation of the polymer.

U.S. Pat. No. 4,888,398 describes polymers based on polyglutamate or polyaspartate, and optionally polyleucine, with pendent groups of the alkoxy-carbonylmethyl type randomly located along the polyamino acid chain. These polyamino acids, grafted with side groups, e.g. methoxycarbonylmethyl groups, can be used in the form of prolonged-release biodegradable implants containing an AP.

U.S. Pat. No. 5,904,936 describes nanoparticles obtained from a polyleucine-polyglutamate block polymer which are capable of forming stable colloidal suspensions and of associating spontaneously with biologically active proteins without denaturing them. The latter can then be released in vivo in a controlled manner over a long period.

U.S. Pat. No. 5,449,513 describes amphiphilic block copolymers comprising a polyoxyethylene block and a polyamino acid block, for example poly(beta-benzyl-L-aspartate). These polyoxyethylene-polybenzylaspartate polymers form micelles capable of encapsulating hydrophobic active molecules such as adriamycin or indomethacin.

Patent application WO-A-99/61512 describes polylysines and polyomithines functionalized with a hydrophobic group (palmitic acid joined to the polylysine or polyomithine) and a hydrophilic group (polyoxyethylene). In the presence of cholesterol, these polymers, e.g. polylysine grafted with polyoxyethylene and palmitoyl chains, form vesicles capable of encapsulating doxorubicin or DNA. These polymers based on polylysines are cationic in a physiological medium.

Patent application WO-A-00/30618 in the name of the Applicant describes poly(sodium glutamate)-poly(methyl, ethyl, hexadecyl or dodecyl glutamate) block or random polymers capable of forming stable colloidal suspensions and of associating spontaneously with biologically active proteins without denaturing them. The latter can then be released in vivo in a controlled manner over a long period. These amphiphilic copolyamino acids are modified by the presence of a hydrophobic alkyl side chain. These alkyl groups are covalently grafted onto the polymer via an ester group. These polymers are anionic in a physiological medium.

Unpublished French patent application no. 02/07008 of Jul. 6, 2002 describes a polyglutamate carrying grafts based on alpha-tocopherol that is bonded to a spacer formed of one to four "amino acid" residues and e.g. one leucine residue.

Thus, although there are a very large number of technical solutions in the prior art which have been developed and proposed for the vectorization of medicinal active principles, it is difficult to find an answer to all the demands and the situation remains unsatisfactory. More specifically, the design of a polyamino acid grafted with hydrophobic groups which is capable of forming a stable colloidal aqueous suspension of vectorization particles suitable for associating reversibly with active principles, and which is inexpensive, is improvable.

In this context, one of the essential objects of the present invention is to provide a novel family of polymers based on polyglutamate and polyaspartate which are anionic at animal physiological pH and which represent an improvement compared with the polymers described in patent application WO-A-00/30618, especially in terms of stability and protein absorption capacity.

Another essential object of the present invention is that these polymers are capable of being used for the vectorization of AP and make it possible optimally to satisfy all the specifications of the specifications sheet, namely, in particular:
- ① capacity:
  - easily and economically to form stable aqueous colloidal suspensions,
  - easily to associate with numerous active principles,
  - and to release these active principles in vivo,
- ① biocompatibility,
- ① biodegradability,
- ① stability to hydrolysis.

This and other objects are achieved by the present invention, which relates first and foremost to a polyamino acid comprising aspartic units and/or glutamic units, some of which carry at least one graft, characterized in that at least one of these grafts:
- is joined to an aspartic or glutamic unit of the main chain by way of a spacer comprising one or more (oligo)amino acids formed of one or more "amino acid" units selected from "amino acid" units having an alkyl or aryl group in the alpha position, preferably from "amino acid" units belonging to the group comprising alanine, valine, leucine, isoleucine and phenylalanine,
- and comprises at least one hydrophobic group:
  - containing at least 6 carbon atoms, preferably from 6 to 30 atoms (e.g. from 8 to 30 carbon atoms),
  - different from alpha-tocopherol,
  - and joined to the spacer by way of at least one ester linkage.

The inventors have improved the known polyamino acids by discovering, surprisingly and unexpectedly, that the grafting, onto these polyamino acids, of grafts comprising hydrophobic groups derived from precursors of the alcohol type are bonded to the polymer via an "(oligo)amino acid" spacer substituted in the alpha position, the stability of the ester linkage in an aqueous medium is greatly improved.

It is to the Applicant's credit to have had the idea of combining, in a totally judicious and advantageous manner, specific biodegradable and anionic polyAsp and/or polyGlu polyamino acids with grafts joined to the polyAsp and/or polyGlu skeleton by an "amino acid" having an alkyl or aryl group in the alpha position.

These novel (co)polymers have proved particularly suitable for the vectorization of proteins.

In one preferred embodiment of the invention, each graft is joined to an aspartic or glutamic unit of the main chain by way of an amide linkage.

As defined in the invention, the term "polyamino acid" covers not only oligoamino acids comprising from 2 to 20 "amino acid" units, but also polyamino acids comprising more than 20 "amino acid" units.

Advantageously, the oligoamino acid or (oligo)amino acids of all or some of the grafts consists (each consist) of mutually identical "amino acid" units.

These polymers have surprising properties of association and/or encapsulation with one or more active principles, compared with analogous products. Furthermore, they are easily degraded in the presence of enzymes to non-toxic catabolites/metabolites (amino acids).

As defined in the invention and throughout the present disclosure, the terms "association" or "associate" employed to qualify the relationships between one or more active principles and the polyamino acids denote in particular that the active principle(s) is (are) bonded to the polyamino acid(s) especially by a weak bond, for example by ionic bonding and/or hydrophobic contact, and/or are encapsulated by the polyamino acid(s).

Preferably, the polyamino acids according to the present invention are oligomers or homopolymers comprising glutamic or aspartic acid repeat units or copolymers comprising a mixture of these two types of "amino acid" units. The units in question in these polymers are amino acids having the D, L or D/L configuration and are bonded via their alpha or gamma positions in the case of the glutamate or glutamic unit and via their alpha or beta positions in the case of the aspartic or aspartate unit.

The preferred "amino acid" units of the main polyamino acid chain are those having the L configuration and a linkage of the alpha type.

Particularly preferably, the polyamino acids according to the invention have general formula (I) below:

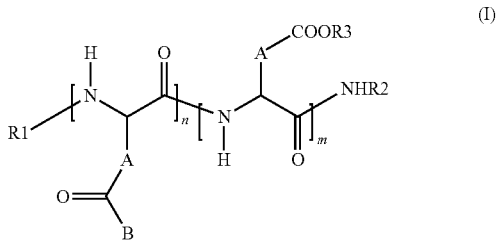

in which:
R1 is H, a linear C2 to C10 or branched C3 to C10 acyl group, or pyroglutamate;
R2 is H, a linear C2 to C10 or branched C3 to C10 alkyl, benzyl or a terminal "amino acid" unit;
R3 is H or $R^{3+}$ is a cationic entity preferably selected from the group comprising:
- metal cations advantageously selected from the subgroup comprising sodium, potassium, calcium and magnesium;
- organic cations advantageously selected from the subgroup comprising:
  - cations based on amine,
  - cations based on oligoamine,
  - cations based on polyamine (polyethylenimine being particularly preferred), and
  - cations based on amino acid(s) advantageously selected from the class comprising cations based on lysine or arginine; and
- cationic polyamino acids advantageously selected from the subgroup comprising polylysine and oligolysine;

the n groups B each independently of one another are a monovalent radical of the formula below:

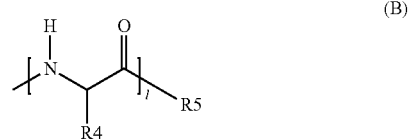

in which:
R4 is methyl(alanine), isopropyl(valine), isobutyl(leucine), sec-butyl (isoleucine) or benzyl(phenylalanine), the amino acids mentioned in brackets being those corresponding to the "amino acid" unit formed when R4 is the alkyl in question;

R5 is a hydrophobic group containing 6 to 30 (e.g. 8 to 30) carbon atoms and preferably bonded to the polymer (more precisely to the spacer [—NH—CHR4—CO—]$_1$), by way of an ester group; and 1 varies from 1 to 6;

A independently is —CH$_2$— (aspartic unit) or —CH$_2$—CH$_2$— (glutamic unit);

n/(n+m) is defined as the molar grafting rate and varies from 0.5 to 100 mol %; and n+m varies from 3 to 1000, preferably between 30 and 300.

Very particularly preferably, a single amino acid (l=1 in formula B above) functionalized with a hydrophobic group is used as the spacer in all or some of the grafts. It has been found that this makes it possible in particular to improve the rates of association of the polyamino acids with active principles.

According to one remarkable characteristic of the invention, all or some of the hydrophobic groups R5 of the grafts are independently selected from the group of radicals comprising:

a linear or branched alkoxy containing from 6 to 30 carbon atoms and capable of containing at least one heteroatom (preferably O and/or N and/or S) and/or at least one unit of unsaturation, an alkoxy containing 6 to 30 carbon atoms, having one or more fused carbocycles and optionally containing at least one unit of unsaturation and/or at least one heteroatom (preferably O and/or N and/or S), and an alkoxyaryl or aryloxyalkyl having 7 to 30 carbon atoms and capable of containing at least one unit of unsaturation and/or at least one heteroatom (preferably O and/or N and/or S).

Even more advantageously, the hydrophobic group of the graft is derived from an alcohol precursor selected from the group comprising octanol, dodecanol, tetradecanol, hexadecanol, octadecanol, oleyl alcohol and cholesterol.

As regards the "amino acid" unit of the graft, the one chosen more especially within the framework of the invention will be an "amino acid" unit derived from the group comprising L-leucine, L-valine and L-phenylalanine.

In a first embodiment of the invention, the main chains of the polyamino acids are alpha-L-glutamate or alpha-L-glutamic homopolymers.

In a second embodiment of the invention, the main chains of the polyamino acids are alpha-L-aspartate or alpha-L-aspartic homopolymers.

In a third embodiment of the invention, the main chains of the polyamino acids are alpha-L-aspartate/alpha-L-glutamate or alpha-L-aspartic/alpha-L-glutamic copolymers.

Advantageously, the distribution of the aspartic and/or glutamic units of the main polyamino acid chain is such that the resulting polymers are either random, or of the block type, or of the multiblock type.

According to another definition, the polyamino acids according to the invention have a molecular weight of between 2000 and 100,000 g/mol, preferably of between 5000 and 40,000 g/mol.

It is furthermore preferable for the molar grafting rate of the polyamino acids according to the invention with hydrophobic units to be between 2 and 70%, preferably between 5 and 40%.

Remarkably, the polyamino acids of the invention can be used in several ways, depending on the grafting rate. The methods of forming a polymer for the encapsulation of an active principle in the various forms envisaged by the invention are known to those skilled in the art. For further details, reference may be made e.g. to the following few references of particular pertinence:

"*Microspheres, Microcapsules and Liposomes; vol 1. Preparation and chemical applications*" Ed. R. Arshady, Citus Books 1999. ISBN: 0-9532187-1-6.

"*Sustained-Release Injectable Products*" Ed. J. Senior and M. Radomsky, Interpharm Press 2000. ISBN: 1-57491-101-5.

"*Colloidal Drug Delivery Systems*" Ed. J. Kreuter, Marcel Dekker, Inc. 1994. ISBN: 0-8247-9214-9.

"*Handbook of Pharmaceutical Controlled Release Technology*" Ed. D. L. Wise, Marcel Dekker, Inc. 2000. ISBN: 0-8247-0369-3.

The polyamino acids are also extremely valuable in that, for a relatively low grafting rate in the order of 3 to 30, they disperse in water at pH 7.4 (e.g. with a phosphate buffer) to give colloidal solutions or suspensions or gels, depending on the polymer concentration and the grafting rate. Furthermore, the polyamino acids (in particulate or non-particulate form) can encapsulate or easily associate with active principles such as proteins, peptides or small molecules. The preferred forming method is the one described in patent application WO-A-00/30618 in the name of the Applicant, which consists in dispersing the polymer in water and incubating the solution in the presence of an AP. This colloidal solution of vectorization particles consisting of the polyamino acids according to the invention can then be filtered on a 0.2 μm filter and then directly injected into a patient.

This particular form according to patent application WO-A-00/30618 can be envisaged especially in the present case, beyond a grafting rate of 30% and depending on the chosen graft. The polymer can then form microparticles capable of associating with or encapsulating AP. In this context the microparticles can be formed by cosolubilizing the AP and the polymer in an appropriate organic solvent and then precipitating the mixture in water. The particles are subsequently recovered by filtration and can then be used for oral administration (in the form of gelatin capsules, in compacted and/or coated form, or else in the form of a dispersion in an oil) or for parenteral administration after redispersion in water.

At grafting rates above 50%, redispersion of the polymer in an aqueous phase becomes more difficult because of the smaller amount of ionizable carboxylate groups, and the polymer precipitates. In this case the polymer can be solubilized in a biocompatible solvent such as N-methylpyrrolidone, or an appropriate oil such as Mygliol®, and then injected by the intramuscular or subcutaneous route or into a tumor. Diffusion of the solvent or oil leads to precipitation of the polymer at the injection site and thus forms a depot. These depots then ensure a controlled release by diffusion and/or by erosion and/or by hydrolytic or enzymatic degradation of the polymer.

Independently of the fact that the microparticulate form of the polyamino acid according to the invention is preferred, the polymers of the invention, in neutral or ionized form, can more generally be used by themselves or in a liquid, solid or gel composition and in an aqueous or organic medium.

It should be understood that the polymer based on polyamino acids contains carboxyl groups which are either neutral (COOH form) or ionized (COO$^-$ anion), depending on the pH and the composition. For this reason the solubility in an aqueous phase is a direct function of the proportion of free COOH in the polymer (not grafted with the hydrophobic unit) and of the pH. In aqueous solution the countercation can be a metal cation such as sodium, calcium or magnesium, or an organic cation such as triethanolamine, tris(hydroxymethyl)aminomethane or a polyamine like polyethylenimine.

The polymers of the invention are obtained e.g. by methods known to those skilled in the art. The random polyamino acids can be obtained by grafting the hydrophobic graft, previously functionalized with the amino acid spacer, directly onto the polymer by means of a conventional coupling reaction. The block or multiblock polyamino acids can be obtained by sequential polymerization of the corresponding amino acid N-carboxy anhydrides (NCA).

For example, a homopolyglutamate or homopolyaspartate polyamino acid or a block, multiblock or random glutamate/aspartate copolymer is prepared by conventional methods.

To obtain a polyamino acid of the alpha type, the most common technique is based on the polymerization of amino acid N-carboxy anhydrides (NCA), which is described e.g. in the article "*Biopolymers*" 1976, 15, 1869, and in the work by H. R. Kricheldorf entitled "*Alpha-amino acid N-carboxy anhydrides and related heterocycles*", Springer Verlag (1987). The NCA derivatives are preferably NCA-O-Me, NCA-O— . . . and/or NCA-O-Bz derivatives (Me=methyl, Et=ethyl and Bz=benzyl). The polymers are then hydrolyzed under appropriate conditions to give the polymer in its acid form. These methods are based on the description given in patent FR-A-2 801 226 in the name of the Applicant. A number of polymers that can be used according to the invention, for example of the poly(alpha-L-aspartic), poly(alpha-L-glutamic), poly(alpha-D-glutamic) and poly(gamma-L-glutamic) types of variable molecular weights, are commercially available. The polyaspartic polymer of the alpha-beta type is obtained by the condensation of aspartic acid (to give a polysuccinimide) followed by basic hydrolysis (cf. Tomida et al., Polymer 1997, 38, 4733-36).

Coupling of the graft with an acid group of the polymer is easily effected by reacting the polyamino acid in the presence of a carbodiimide as coupling agent, and optionally a catalyst such as 4-dimethylaminopyridine, in an appropriate solvent such as dimethylformamide (DMF), N-methylpyrrolidone (NMP) or dimethyl sulfoxide (DMSO). The carbodiimide is e.g. dicyclohexylcarbodiimide or diisopropylcarbodiimide. The grafting rate is controlled chemically by the stoichiometry of the constituents and reactants or by the reaction time. The hydrophobic grafts functionalized with an amino acid are obtained by conventional peptide coupling or by direct condensation under acid catalysis. These techniques are well known to those skilled in the art.

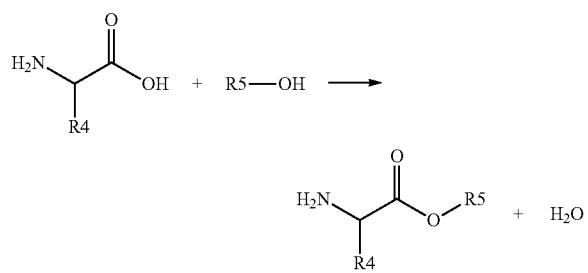

Block or multiblock copolymer is synthesized using NCA derivatives previously synthesized with the hydrophobic graft. The synthesis scheme is as follows:

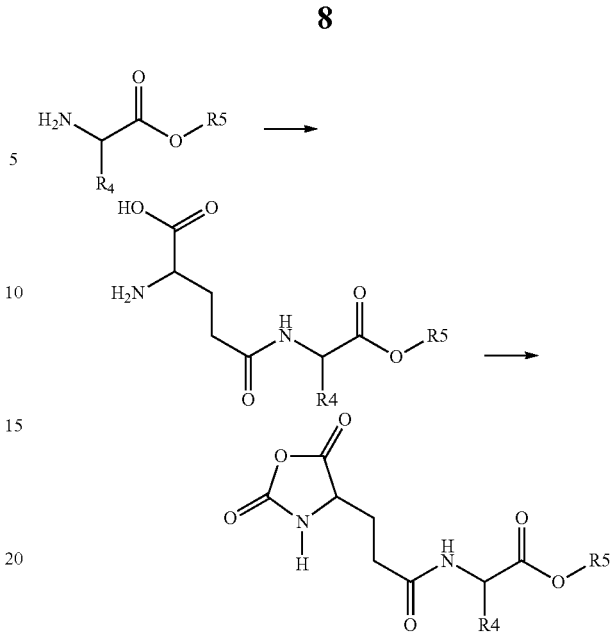

Preferably, the NCA/hydrophobic graft derivative is copolymerized with NCA-O-benzyl and the benzyl groups are then removed selectively by hydrolysis.

According to another of its features, the invention relates to a pharmaceutical, cosmetic, dietetic or phytosanitary composition comprising at least one polyamino acid as defined above and optionally at least one active principle, which can be a therapeutic, cosmetic, dietetic or phytosanitary active principle.

According to one valuable provision of the invention, the active principle is associated with the polyamino acid(s) by one or more bonds other than covalent chemical bonds.

The techniques of associating one or more AP with the grafted polyamino acids according to the invention are described in particular in patent application WO-A-00/30618. They consist in incorporating at least one active principle into the liquid medium containing particles VP to give a colloidal suspension of VP laden or associated with one or more active principles AP. This incorporation, which results in the AP being trapped by the VP, can be effected in the following manner:
  introduction of AP into aqueous solution, followed by addition of VP, either in the form of a colloidal suspension or in the form of isolated VP (lyophilizate or precipitate); or
  addition of AP, either in solution or in the pure or preformulated state, to a colloidal suspension of particles VP, optionally prepared for immediate use by dispersion of dry VP in an appropriate solvent such as water.

Preferably, the active principle is a protein, a glycoprotein, a protein bonded to one or more polyalkylene glycol chains (preferably polyethylene glycol (PEG) chains: "PEGylated protein"), a polysaccharide, a liposaccharide, an oligo-nucleotide, a polynucleotide or a peptide.

In one variant, the active principle is a "small" hydrophobic, hydrophilic or amphiphilic organic molecule.

As defined in the present disclosure, a "small" molecule is especially a small non-protein molecule.

The following may be mentioned as examples of AP that can be associated with the polyamino acids according to the invention, whether or not they are in the form of nanoparticles or microparticles:

① proteins such as insulin, interferons, growth hormones, interleukins, erythropoietin or cytokines;
① peptides such as leuprolide or cyclosporin;
① small molecules such as those belonging to the anthracycline, taxoid or camptothecin family;
① and mixtures thereof.

In one embodiment the composition of the invention is in the form of a gel, a solution, a suspension, an emulsion, micelles, nanoparticles, microparticles, an implant, a powder or a film.

In one of its particularly preferred forms, the composition, whether or not laden with active principle(s), is a stable colloidal suspension of nanoparticles and/or microparticles and/or micelles of polyamino acids in an aqueous phase.

In another embodiment the composition of the invention is in the form of a solution in a biocompatible solvent and can be injected by the subcutaneous or intramuscular route or into a tumor.

If the composition according to the invention is a pharmaceutical composition, it can be administered by the oral, parenteral, nasal, vaginal, ocular, subcutaneous, intravenous, intramuscular, intradermal, intraperitoneal, intracerebral or buccal route.

It is also possible to envisage a composition in the form of a solution in a biocompatible solvent that can be injected by the subcutaneous or intramuscular route or into a tumor.

In another variant the composition according to the invention is formulated in such a way that it is capable of forming a depot at the injection site.

The invention further relates to compositions which comprise polyamino acids according to the invention and active principles and which can be used for the preparation of:
drugs, particularly for administration by the oral, nasal, vaginal, ocular, subcutaneous, intravenous, intramuscular, intradermal, intraperitoneal or intracerebral route, it being possible in particular for the active principles of these drugs to be proteins, glycoproteins, proteins bonded to one or more polyalkylene glycol chains {e.g. polyethylene glycol (PEG) chains, in which case the term "PEGylated" proteins is used}, peptides, polysaccharides, liposaccharides, oligonucleotides, polynucleotides and small hydrophobic, hydrophilic or amphiphilic organic molecules;
and/or nutriments;
and/or cosmetic or phytosanitary products.

According to yet another of its features, the invention relates to a process for the preparation of:
drugs, particularly for administration by the oral, nasal, vaginal, ocular, subcutaneous, intravenous, intramuscular, intradermal, intraperitoneal or intracerebral route, it being possible in particular for the active principles of these drugs to be proteins, glycoproteins, proteins bonded to one or more polyalkylene glycol chains {e.g. polyethylene glycol (PEG) chains, in which case the term "PEGylated" proteins is used}, peptides, polysaccharides, liposaccharides, oligonucleotides, polynucleotides and small hydrophobic, hydrophilic or amphiphilic organic molecules;
and/or nutriments;
and/or cosmetic or phytosanitary products,
said process being characterized in that it consists essentially in using at least one polyamino acid as defined above and/or the composition also described above.

The invention further relates to a method of therapeutic treatment that consists essentially in administering the composition as described in the present disclosure by the oral, parenteral, nasal, vaginal, ocular, subcutaneous, intravenous, intramuscular, intradermal, intraperitoneal, intracerebral or buccal route.

In one particular variant of the invention, said method of therapeutic treatment consists essentially in administering the composition as described above, in the form of a solution in a biocompatible solvent, and then injecting it by the subcutaneous or intramuscular route or into a tumor, preferably in such a way that it forms a depot at the injection site.

The invention will be better understood and its advantages and variants will become clearly apparent from the Examples below, which describe the synthesis of the polyamino acids grafted with a hydrophobic group, their conversion to an AP vectorization system (stable aqueous colloidal suspension) and the demonstration of the ability of such a system to associate with a protein to form pharmaceutical compositions.

EXAMPLE 1

Preparation of Polymer P1

Synthesis of a Polyglutamate Grafted with a Grafted LeuOC12

1/Structure of the Graft:

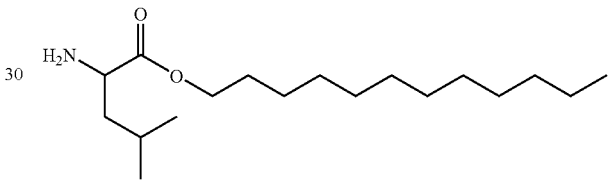

This product is synthesized from L-leucine and dodecanol by condensation in the presence of an acid, according to a process described in patent U.S. Pat. No. 4,826,818.

2/Synthesis of the Polymer:

The alpha-L-polyglutamic polymer (having a molecular weight equivalent to about 12,000 g/mol, relative to a polyoxyethylene standard) is obtained by the polymerization of monomers consisting of N-carboxy anhydride derivatives of methyl glutamate: NCAGluOMe. This polymerization is followed by hydrolysis, as described in patent application FR-A-2 801 226. 18 g of the polymer are then dissolved in 360 ml of dimethylformamide (DMF) by heating at 80° C. for 2 hours. Once the polymer is solubilized, the temperature is allowed to drop to 25° C. and 5.0 g of the graft LeuOCl2, previously solubilized in 9 ml of DMF, 0.5 g of 4-dimethylaminopyridine, previously solubilized in 5 ml of DMF, and 3.16 g of diisopropylcarbodiimide are added in succession. After 6 hours at 25° C., with stirring, the reaction medium is poured into 720 ml of water containing 15% of sodium chloride and hydrochloric acid (pH 2). The precipitated polymer is then recovered by filtration and washed with 0.1 N hydrochloric acid and then with diisopropyl ether. The polymer is subsequently dried in an oven under vacuum at 40° C. to give a yield in the order of 90%. The grafting rate estimated by proton NMR is about 11.6%.

EXAMPLE 2

Preparation of Polymers P2 to P5, C1 and C2

Polymers P2 to P5 and Comparative Examples C1 and C2 are synthesized according to the same protocol as for polymer P1. For the graft ValChol we coupled cholesterol with Boc-valine in the presence of diisopropylcarbodiimide and then deprotected the amine in an acid medium (cf., for example, the work "Principles of peptide synthesis" by Bodanszky, Springer-Verlag 1984).

EXAMPLE 3

Characteristics of the Polymers

EXAMPLE 4

Study of Association with Insulin

An aqueous solution of pH 7.4 containing 10 mg of polymer per milliliter and 200 IU of insulin (7.4 mg) is prepared. The solutions are incubated for two hours at room temperature and the free insulin is separated from the associated insulin by ultrafiltration (cut-off at 100 kDa, 15 minutes under 10,000 G at 18° C.). The free insulin recovered from the

TABLE 1

| Polymer | Graft | Structure of graft [1] | Mol % of graft [2] | Mn g/mol [3] |
|---|---|---|---|---|
| P1 | L-LeuOC12 | | 11.6 | 13,500 |
| P2 | L-LeuOC8 | | 14.7 | 14,000 |
| P3 | L-ValOC12 | | 11.8 | 15,700 |
| P4 | L-PheOC12 | | 10.4 | 11,000 |
| P5 | L-ValChol | | 5.5 | 13,300 |
| C1 | OC12 | | 15.3 | 10,500 |
| C2 | (L-Leu)$_3$NH$_2$ | | 21.0 | — |

[1] The bond shown as a dotted line represents the bond to the polymer.
[2] The mol % of grafting is estimated by proton NMR of the polymer solubilized in deuterated trifluoroacetic acid.
[3] Mn is the number-average molecular weight measured by size exclusion chromatography using a mixture of PBS (pH 7.4) and acetonitrile as the eluent, and is given relative to a polyoxyethylene standard.

filtrate is then measured quantitatively by HPLC (high performance liquid chromatography) and the amount of associated insulin is deduced. The results are given in Table 2 below.

TABLE 2

| Polymer | % association |
|---------|---------------|
| P1 | 97% |
| P2 | 92% |
| P3 | 97% |
| P5 | 98% |
| C1 | 75% |
| C2 | 55% |

The results demonstrate that the insulin association rates of the polymers of the invention are higher than those of polymers not having an "amino acid" spacer (C1) or having a hydrophobic amino acid sequence but no hydrophobic group of the linear or polycyclic alkyl type (C2).

EXAMPLE 5

Study of the Stability of the Polymers in an Aqueous Medium

The polymers are solubilized in water at 20 mg/ml, the pH being adjusted to 6.0, and the clear solutions are then placed in thermostatically controlled ovens at 25 or 37° C. for one week. The pH range that is useful in the intended applications is often between 6 and 7.4. We chose a pH of 6 for this study in order to accelerate the degradation kinetics. Analysis of the polymers by various techniques shows that the only degradation path of the polymer under these conditions is hydrolysis of the ester grafts. The hydrolysis rate of polymers P1, P3 and C1 as a function of time is given in Table 3 below.

TABLE 3

| Polymer | % hydrolysis 1 week at 25° C. | % hydrolysis 1 week at 37° C. |
|---------|-------------------------------|-------------------------------|
| P1 | 0.94% | 1.91% |
| P3 | 0.01% | 0.30% |
| C1 | 1.63% | 4.31% |

These results show that, in addition to having a higher insulin adsorption capacity, P1 and P3 are more stable to hydrolysis.

The invention claimed is:

1. Polyamino acid comprising aspartic residues and/or glutamic residues, wherein said polyamino acid has general formula (I) below:

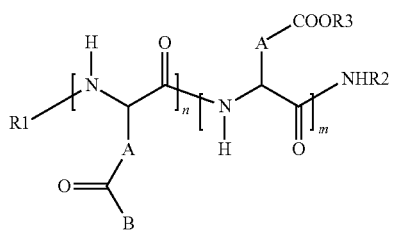

in which:
R1 is selected from the group consisting of: H, a linear C2 to C10 acyl group, a branched C3 to C10 acyl group, and pyroglutamate;
R2 is selected from the group consisting of: H, a linear C2 to C10 alkyl group, a branched C3 to C10 alkyl, benzyl and a C- terminal "amino acid" unit;
R3 is H, or R3$^+$is a cationic entity selected from the group consisting of: metal cations, sodium cation, potassium cation, calcium cation, magnesium cation, cations based on amine, cations based on oligoamine, cations based on polyamine, polyethylenimine, cations based on amino acid(s), cations based on lysine, cations based on arginine, polylysine and oligolysine; the n B groups are independently:

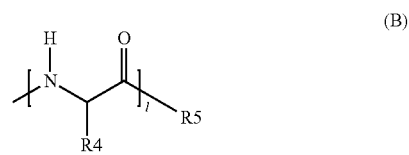

in which: each R4 is selected from the group consisting of: methyl, isopropyl, isobutyl, sec-butyl and benzyl;
each R5 is a hydrophobic group, excluding alpha-tocopheryloxy, wherein the hydrophobic group is an alcohol precursor selected from the group consisting of octanol, dodecanol, tetradecanol, hexadecanol, octa-decanol, oleyl alcohol and cholesterol;
and l equals 1;
A is —CH$_2$— or —CH$_2$CH$_2$—;
the molar grafting rate n/(n+m) is 0.5 to 100 mol %; and
n+m varies from 3 to 1000.

2. Polyamino acid according to claim 1 wherein the at least one hydrophobic group R5 is independently selected from the group of radicals consisting of:
a linear or branched alkoxy containing from 6 to 30 carbon atoms and containing at least one heteroatom, and/or at least one unit of unsaturation, an alkoxy containing 6 to 30 carbon atoms, having one or more fused carbocycles and an alkoxyaryl or aryloxyalkyl containing 7 to 30 carbon atoms and containing at least one unit of unsaturation and/or at least one heteroatom.

3. Polyamino acid according to claim 1, characterized in that the "amino acid" unit of R2 is selected from the group consisting of L-leucine, L-valine, L-phenylalanine and mixtures thereof.

4. Polyamino acid according to claim 1, characterized in that the at least one aspartic or glutamic residue of the main chain comprises an alpha-L-glutamate or alpha-L-glutamic homopolymer.

5. Polyamino acid according to claim 1, characterized in that the at least one residue aspartic or glutamic residue of the main chain comprises an alpha-L-aspartate or alpha-L-aspartic homopolymer.

6. Polyamino acid according to claim 1, characterized in that the at least one residue aspartic or glutamic residue of the main chain comprises an alpha-L-aspartate /alpha-L-glutamate or alpha-L-aspartic/alpha-L-glutamic copolymer.

7. Polyamino acid according to claim 1, characterized in that its molecular weight is between 2000 and 100,000 g/mol.

8. Polyamino acid according to claim 1, characterized in that the molar grafting rate is between 2 and 70.

9. Pharmaceutical, cosmetic, dietetic or phytosanitary composition comprising at least one polyamino acid according to claim 1.

10. Composition according to claim 9, wherein said composition comprises at least one active principle.

11. Composition according to claim 10, wherein said active principle is associated with the polyamino acid(s) by one or more bonds other than covalent chemical bonds.

12. Composition according to claim 10, wherein said at least one active principle is selected from the group consisting of:
a protein, a glycoprotein, a protein bonded to one or more polyalkylene glycol chains, polyethylene glycol (PEG) chains, a polysaccharide, a liposaccharide, an oligonucleotide, a polynucleotide and a peptide.

13. Composition according to claim 9 wherein said at least one active principle is a hydrophobic, hydrophilic or amphiphilic organic molecule.

14. Composition according to claim 9 wherein said composition is a colloidal suspension of nanoparticles, microparticles or micelles of the polyamino acid(s) in an aqueous phase.

15. Composition according to claim 9 wherein said composition is in a form selected from the group consisting of:
a solution, a gel, a suspension, an emulsion, micelles, nanoparticles, microparticles, an implant, a powder and a film.

16. Composition according to claim 9 wherein said composition is administered by a route selected from the group consisting of:
oral, parenteral, nasal, vaginal, ocular, subcutaneous, intravenous, intramuscular, intradermal, intraperitoneal, intracerebral and buccal route.

17. Composition according to claim 9 wherein said composition is in the form of a solution in a biocompatible solvent and is capable of being injected by the subcutaneous or intramuscular route or into a tumor.

18. Composition according to claim 9 wherein said composition is injectable and is capable of forming a depot at the injection site.

19. Composition according to claim 13, wherein said composition is characterized in that it is intended for the preparation of drugs, selected from the group consisting of: proteins, glycoproteins, proteins bonded to one or more polyalkylene glycol chains, polyethylene glycol (PEG) chains, peptides, polysaccharides, liposaccharides, oligonucleotides, polynucleotides and small hydrophobic, hydrophilic organic molecules, amphiphilic organic molecules; nutriments; cosmetic and phytosanitary products.

20. Process for the preparation of drugs, characterized in that it comprises using at least one polyamino acid according to claim 3.

21. The polyamino acid of claim 1, wherein n+m is 30 to 300.

* * * * *